United States Patent [19]
Gallegos

[11] Patent Number: 6,132,017
[45] Date of Patent: Oct. 17, 2000

[54] REINFORCED ARTICLE OF FURNITURE

[76] Inventor: Ramon Gallegos, 4740 E. Sunrise Dr., #206, Tucson, Ariz. 85718

[21] Appl. No.: 09/073,446

[22] Filed: May 5, 1998

[51] Int. Cl.[7] .................................................. A47B 96/18
[52] U.S. Cl. ........................ 312/140.1; 312/245; 312/264
[58] Field of Search .................................. 52/653.1, 657, 52/695; 312/257.1, 140.1, 245, 264, 265; 108/161, 59; 211/191

[56] References Cited

U.S. PATENT DOCUMENTS

| | | | |
|---|---|---|---|
| 1,994 | 2/1841 | Price et al. ................................. | 52/695 |
| 442,468 | 12/1890 | Wegener .................................... | 108/59 |
| 2,965,428 | 12/1960 | Jacobs et al. ............................. | 312/245 |
| 4,190,001 | 2/1980 | Cecala ....................................... | 108/161 |
| 5,592,789 | 1/1997 | Liddell, Sr. et al. ........................ | 52/63 |

FOREIGN PATENT DOCUMENTS

| | | | |
|---|---|---|---|
| 1002384 | 3/1952 | France ................................. | 312/265.4 |
| 1386976 | 12/1964 | France ................................. | 312/265.5 |

*Primary Examiner*—Peter M. Cuomo
*Assistant Examiner*—Jerry Anderson
*Attorney, Agent, or Firm*—Antonio R. Durando

[57] ABSTRACT

An article of furniture includes two supports each of which is made up of a shelf mounted on a rectangular frame. The supports are spaced from one another by pairs of vertical boards which bracket X-shaped spacers constituted by inclined interlocking boards.

1 Claim, 3 Drawing Sheets

REINFORCED ARTICLE OF FURNITURE

BACKGROUND OF THE INVENTION

1. Field of the Invention

The invention relates to furniture.

2. Description of the Prior Art

Most homes have one or more articles of furniture such as bookcases, entertainment centers, china closets and hutches. This furniture is sometimes subjected to actions not anticipated during design of the furniture. For instance, children may climb onto the furniture or the furniture may undergo an earthquake.

When the furniture is subjected to these or other unanticipated actions, the furniture may break or tip. This can result not only in damage to the home and the articles held by the furniture but, more importantly, in injury to the occupants of the home and even death as has been documented.

SUMMARY OF THE INVENTION

It is an object of the invention to improve the sturdiness of furniture.

Another object of the invention is to improve the stability of furniture.

The preceding objects, as well as others which will become apparent as the description proceeds, are achieved by the invention.

One aspect of the invention resides in an article of furniture. The article of furniture comprises a pair of supports, and means spacing the supports from one another. The spacing means includes at least one spacing unit having an X-shaped portion. Preferably, at least one of the supports comprises a shelf.

The X-shaped portion of the spacing means allows a rigidifying or bracing effect to be obtained. This, in turn, enables the sturdiness and stability of the furniture article to be enhanced.

Another aspect of the invention resides in a structure. The structure comprises a wall including at least one stud, and an article of furniture adjacent the wall. The furniture article includes a pair of supports, and means spacing the supports from one another. The spacing means comprises at least one spacing unit having an X-shaped portions, and the furniture article is connected to the stud at the location of the spacing unit. It is preferred for at least one of the supports to include a shelf.

As indicated above, the X-shaped portion of the spacing means is capable of producing strengthening and stabilizing effects. By attaching the furniture article to a wall stud at the location of the X-shaped portion, the furniture article can be firmly anchored to increase the stability thereof.

An additional aspect of the invention resides in a method of making an article of furniture. The method comprises the steps of providing a pair of supports, and spacing the supports using at least one spacing unit having an X-shaped portion.

The spacing unit can include a pair of members which cross one another, and one of the members may have a first end adjacent one of the supports while the other of the members may have a second end adjacent the other of the supports. The method can here further comprise the steps of positioning an additional member so as to extend between the first and second ends, and securing the additional member to at least one of the supports.

Other features and advantages of the invention will be forthcoming from the following detailed description of certain preferred embodiments when read in conjunction with the accompanying drawings.

DESCRIPTION OF THE PREFERRED EMBODIMENTS

Figure 1:
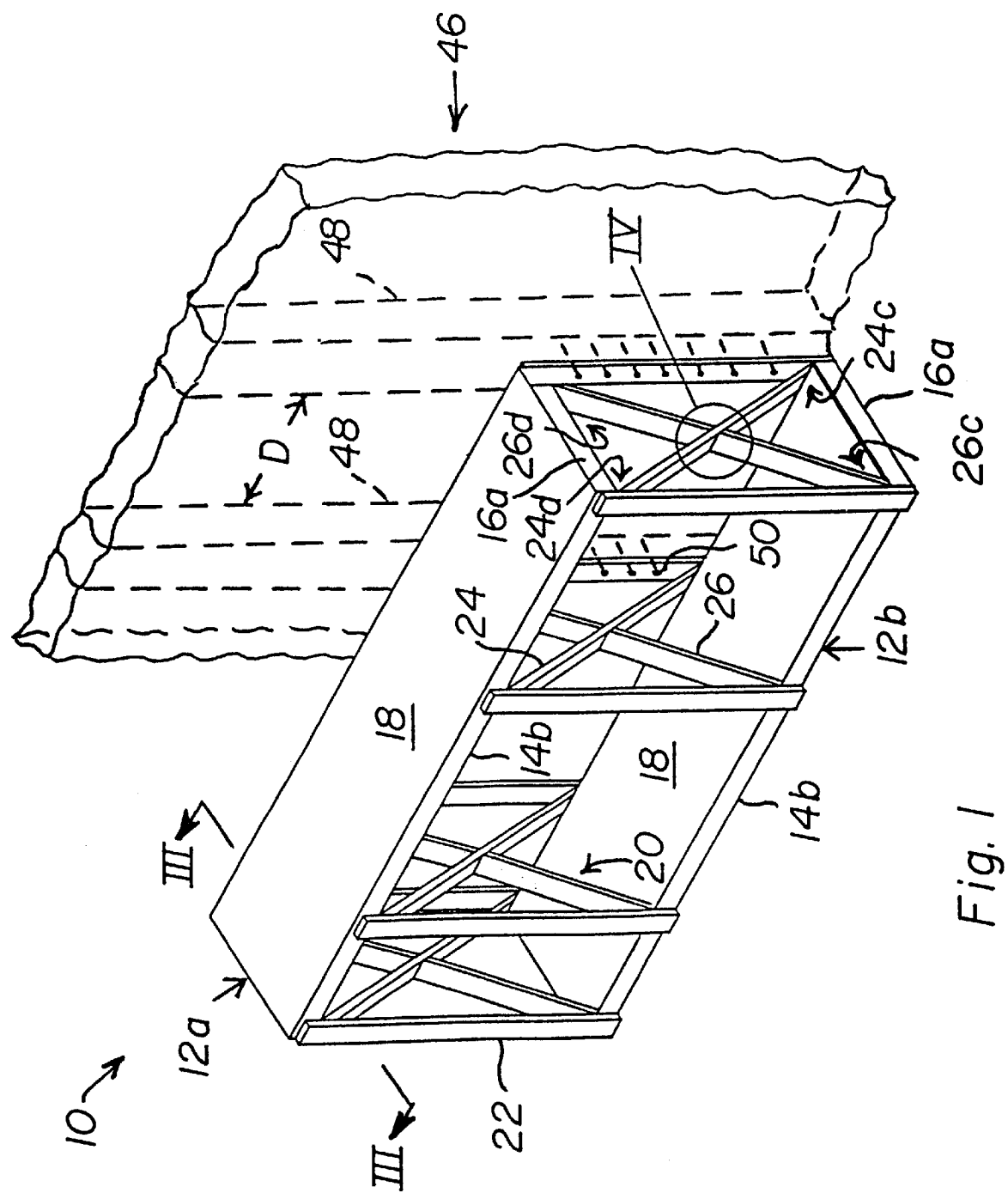
FIG. 1 is a perspective view of an article of furniture in accordance with the invention.
Figure 2:
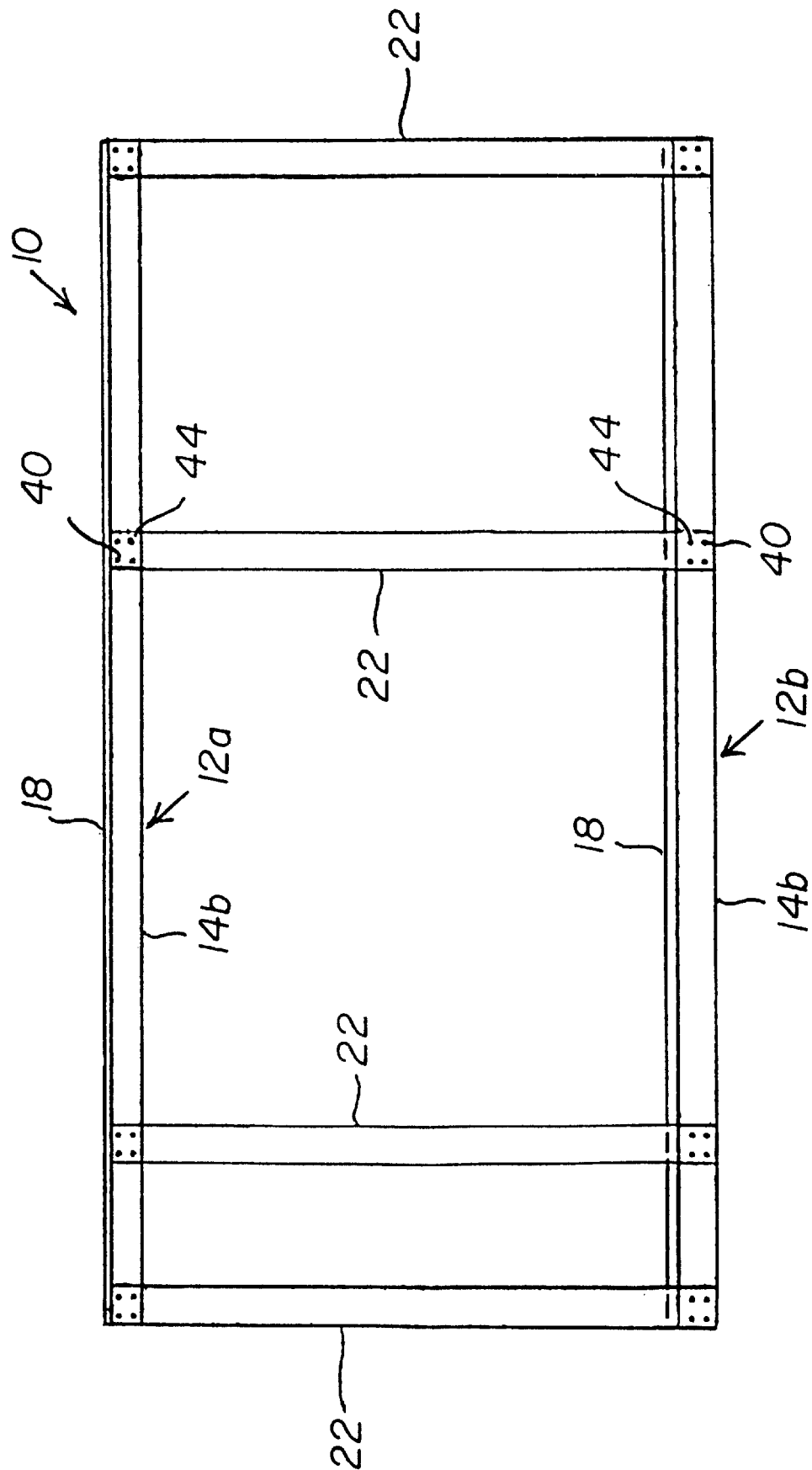
FIG. 2 is a side view of the furniture article of FIG. 1.
Figure 3:
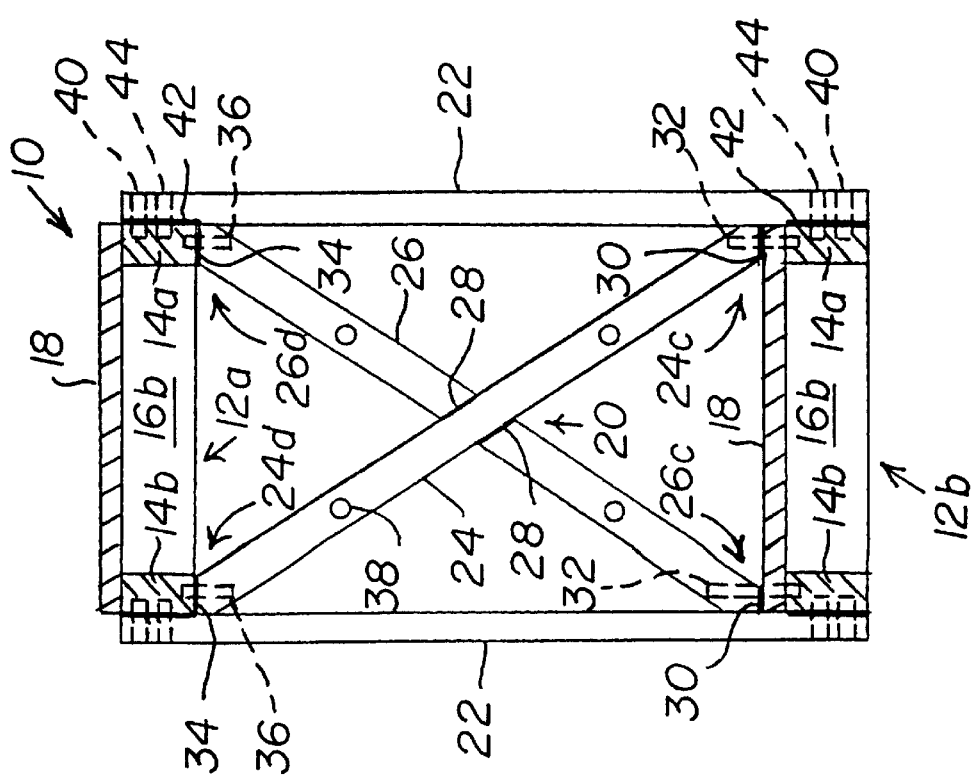
FIG. 3 is a sectional view of the furniture article as seen in the direction of the arrows III—III of FIG. 1.

Referring to FIGS. 1–3, an article of furniture according to the invention is identified by the numeral 10. The furniture article 10 is here an entertainment center but could also be any of a variety of other types of furniture. For instance, the furniture article 10 could also be a hutch, a china closet or a bookcase.

The furniture article 10 comprises a pair of supports or carriers 12a and 12b. The supports 12a,12b are identical and only the support 12a will be described. The reference characters used for the support 12a apply to the support 12b as well.

The furniture article 10 is elongated, and the support 12a includes a horizontal rectangular frame having two spaced parallel frame members 14a and 14b. The frame members 14a,14b, which are in the form of boards, extend lengthwise of the furniture article 10. The frame further has two spaced parallel frame members 16a and 16b which are again in the form of boards. The frame boards 16a,16b, which are shorter than the frame boards 14a,14b, extend widthwise of the furniture article 10. The shorter frame boards 16a,16b are located at opposite longitudinal ends of the furniture article 10 and bridge the longer frame boards 14a,14b.

The shorter frame boards 16a,16b are preferably connected to the longer frame boards 14a,14b by nails and adhesive, e.g., glue.

The support 12a additionally includes a support panel or carrier panel 18 constituting a shelf. The shelf 18 is mounted on top of the frame defined by, and rests on the upper surfaces of, the frame boards 14a,14b,16a,16b. The shelf 18 can be nailed to the frame boards 14a,14b,16a,16b and also bonded thereto by an adhesive such as glue.

The support 12a overlies and is vertically spaced from the support 12b. The supports 12a,12b are held apart by four X-shaped spacing units 20 and eight vertical spacing members 22 in the form of boards.

The spacing units 20 are spaced from one another lengthwise of the furniture article 10. Each of the spacing units 20 comprises two elongated legs or members 24 and 26 which cross one another and are in the form of boards.

Figure 4:
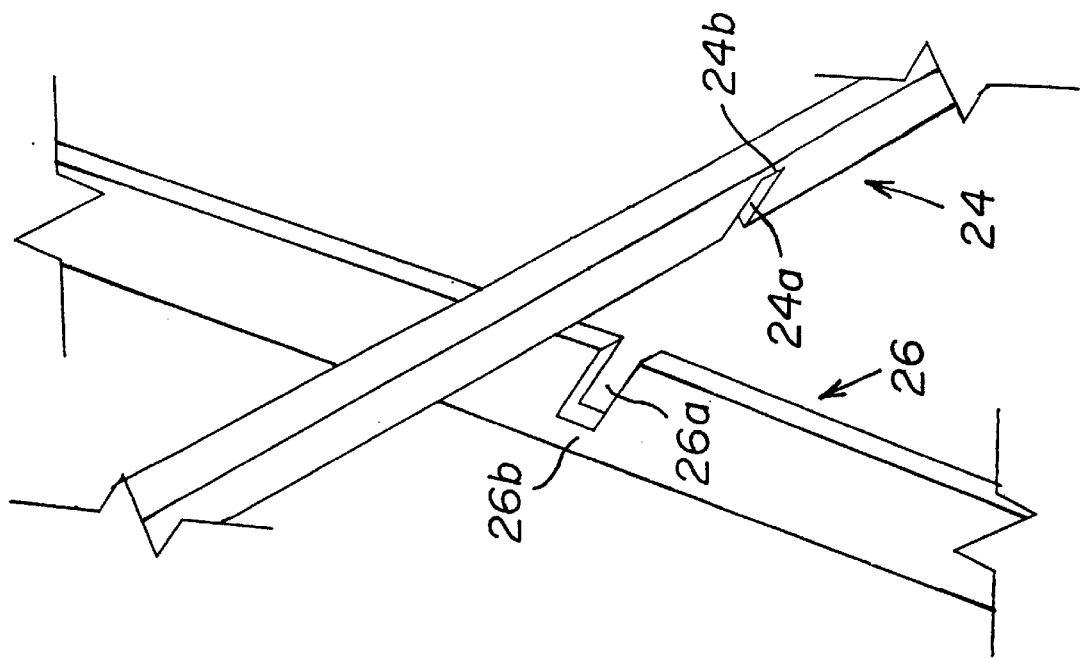
FIG. 4 is an enlarged exploded perspective view of the circled area IV of FIG. 1.

As shown in FIG. 4, each spacing board 24 is provided with a notch or cutout 24a midway along its length. Similarly, each spacing board 26 is provided with a notch or cutout 26a midway along the length thereof. The notches 24a,26a extend across the thicknesses and partway across the widths of the spacing boards 24,26. Each notch 24a runs from one longitudinal edge of the respective spacing board 24 partway to the opposite longitudinal edge, and such opposite longitudinal edge is separated from the notch 24a by a web or bridging portion 24b of the spacing board 24. Likewise, each notch 26a runs from one longitudinal edge of the respective spacing board 26 partway to the opposite longitudinal edge, and the latter edge is separated from the notch 26a by a web or bridging portion 26b of the spacing board 26. The notches 24a,26a are open at both sides and at one longitudinal edge of the respective boards 24,26.

The notch 24a of a spacing board 24 is designed to receive the web 26b of the associated spacing board 26 with a relatively close fit. Similarly, the notch 26a of a spacing board 26 is designed to receive the web 24b of the associated spacing board 24 with a relatively close fit.

To assemble a spacing unit 20, an adhesive, e.g., glue, is applied to the surfaces bounding the notch 24a and/or 26a. The respective spacing boards 24,26 are then positioned so that they cross each other and the notches 24a,26a face one another. This is illustrated in FIG. 4. The spacing boards 24,26 are now moved towards each other such that the web 26b of the spacing board 26 enters the notch 24a of the spacing board 24 and the web 24b of the spacing board 24 enters the notch 26a of the spacing board 26. The webs 24b,26b are pushed towards one another until the continuous and discontinuous longitudinal edges of the spacing board 24 respectively are in the same planes as the discontinuous and continuous longitudinal edges of the spacing board 26. The adhesive applied to the surfaces bounding the notch 24a and/or 26a dries to form bonding layers 28 (FIG. 3) between the spacing boards 24,26.

Once the spacing units 20 have been assembled, the spacing units 20 are placed on the shelf 18 of the lower support 12b. The spacing boards 24 have lower ends 24c (FIGS. 1 and 3) which sit on the lower shelf 18 adjacent one of the longitudinal edges of the lower support 12b while the spacing boards 26 have lower ends 26c (FIGS. 1 and 3) which sit on the lower shelf 18 adjacent the other longitudinal edge of the lower support 12b. An adhesive, e.g., glue, is applied to the lower spacing board ends 24c,26c and/or to the lower shelf 18 prior to placing the spacing units 20 on the lower shelf 18. When the spacing units 20 have been positioned on the lower shelf 18, nails are driven through the lower spacing board ends 24c,26c, and through the lower shelf 18, into the frame 14a,14b,16a,16b of the lower support 12b. The adhesive is allowed to set or dry so that bonding layers 30 (FIG. 3) are formed between the spacing boards 24,26 and the lower shelf 18. Subsequent to setting or drying of the adhesive, the spacing boards 24,26 are additionally connected to the lower frame 14a,14b,16a,16b by screws 32 (FIG. 3) passing through the lower spacing board ends 24c,26c, and through the lower shelf 18, into the lower frame 14a,14b,16a,16b.

The spacing boards 24 have upper ends 24d (FIGS. 1 and 3) and the spacing boards 26 upper ends 26d (FIGS. 1 and 3). The bottom edge of the frame 14a,14b,16a,16b of the upper support 12a is placed on the upper spacing board ends 24d,26d such that the latter are adjacent the longitudinal edges of the support 12a. An adhesive, e.g., glue, is applied to the upper spacing board ends 24d,26d and/or to the bottom edge of the upper frame 14a,14b,16a,16b before the upper support 12a is positioned on the spacing boards 24,26. Once the upper support 12a has been placed on the spacing boards 24,26, nails are driven into the upper spacing board ends 24d,26d and the upper frame 14a,14b,16a,16b. The adhesive is then allowed to set or dry so that the adhesive forms bonding layers 34 (FIG. 3) between the spacing boards 24,26 and the upper frame 14a,14b,16a,16b. After the adhesive has set or dried, the upper spacing board ends 24d,26d are screwed to the upper frame 14a,14b,16a,16b by screws 36 (FIG. 3).

The spacing units 20 span the supports 12a,12b widthwise, that is, the spacing units 20 extend across the widths of the supports 12a,12b.

Referring to FIG. 3, those longitudinal edges of a spacing unit 20 which face a neighboring spacing unit 20 may be formed with holes or recesses 38. The holes 38 are designed to receive holding or mounting elements, e.g., dowel pins, for shelves to be mounted between the shelves 18. In the spacing unit 20 shown in FIG. 3, the visible longitudinal edge of each spacing board 24,26 is provided with one hole 38 on either side of the intersection of the boards 24,26. The holes 38 are here equidistant from the intersection.

Considering FIG. 1, two of the spacing boards 22 bracket each of the spacing units 20. Thus, four of the eight spacing boards 22 are located on one side of the furniture article 10 and extend between the lower ends 24c of the spacing boards 24 and the upper ends 26d of the spacing boards 26. The remaining spacing boards 22 are located on the opposite side of the furniture article 10 and extend between the lower ends 26c of the spacing boards 26 and the upper ends 24d of the spacing boards 24.

To mount the spacing boards 22, an adhesive, e.g., glue, is applied to the ends of the spacing boards 22 and/or to the outer peripheral edges of the supports 12a,12b adjacent the ends 24c,24d,26c,26d of the spacing boards 24,26. The spacing boards 22 are then positioned alongside the spacing units 20 and against the outer peripheral edges of the supports 12a,12b so that the spacing boards 22 bridge the supports 12a,12b. Each of the spacing boards 22 is now secured to the frames 14a,14b,16a,16b of the supports 12a,12b by nails 40 (FIGS. 2 and 3). The adhesive applied to the spacing boards 22 and/or to the outer edges of the supports 12a,12b is allowed to set or dry so that bonding layers 42 (FIG. 3) are formed between the spacing boards 22 and the frames 14a,14b,16a,16b. Once the adhesive has set or dried, the spacing boards 22 are screwed to the frames 14a,14b,16a,16b by screws 44 (FIGS. 2 and 3).

FIG. 1 shows the furniture article 10 sitting against a wall 46 of a structure such as, for example, a house. The wall 46 includes a pair of studs 48 which are spaced from one another by a distance, D.

The rightmost spacing unit 20 of the furniture article 10 in FIG. 1 is separated from the next spacing unit 20 by the same distance, D, separating the studs 48. The furniture article 10 is positioned with the rightmost spacing unit 20 adjacent the right stud 48, the next spacing unit 20 adjacent the left stud 48, and the spacing boards 22 running between the spacing board ends 24c,26d of the two rightmost spacing units 20 abutting the wall 46. These spacing boards 22 are anchored to the respective studs 48 by anchoring elements 50 such as screws.

The frame boards 14a,14b,16a,16b and the spacing boards 22,24,26 preferably consist of hardwood. The shelves 18 may, for instance, be made of plywood.

The furniture article 10 has high strength and good stability because the X-shaped spacing units 20 brace and rigidify the furniture article 10. The interlock formed by the notches 24a,26a and the webs 24b,26b enhances the strengthening effect of the spacing units 20.

The strength of the furniture article 10 is increased further by the triple connections (adhesive, nails, screws) between the spacing units 20, as well as the spacing boards 22, and the frames 14a,14b,16a,16b of the respective supports 12a, 12b.

An additional increase in the strength of the furniture article 10 is obtained by making the frame boards 14a,14b, 16a,16b and the spacing boards 22,24,26 of hardwood.

Anchoring of the furniture article 10 to the wall 46 allows even greater stability of the furniture article 10 to be achieved.

Various modifications are possible within the meaning and range of equivalence of the appended claims.

I claim:

1. An article of furniture for use against a wall having at least a pair of equally spaced studs which are spaced by a stud-to-stud distance, said article comprising:

a first support including a pair of spaced first longitudinal members having upward, sideways and downward facing surfaces and a first shelf mounted on said upward facing surfaces of said first longitudinal members;

a second support above said first support, said second support including a pair of spaced second longitudinal members having upward, sideways and downward facing surfaces and a second shelf mounted on said upward facing surfaces of said second longitudinal members; and at least two means spacing said supports from one another, each of said spacing means including an x-shaped portion having a pair of elongated members which cross one another, each of said elongated members bridging said first and second supports, and one of said elongated members having a first end secured to said downward facing surface of one of said second longitudinal members and an additional end secured to said upward facing surface of one of said first longitudinal members, the other of said elongated members having a first end secured to said upward facing surface of the other of said first longitudinal members and an additional end secured to said downward facing surface of the other of said second longitudinal members, and a pair of spacing members, a first spacing member which bridges said first end of said one elongated member and said first end of said other elongated member and is secured to said sideways facing surfaces of one of said first longitudinal members and one of said second longitudinal members, and a second spacing member which bridges said additional end of said one elongated member and said additional end of said other elongated member and is secured to said sideways facing surfaces of the other of said first longitudinal members and the other end of said second longitudinal members, said spacing means being equally spaced by said stud-to-stud distance to allow connection of said spacing means to said studs.

* * * * *